United States Patent
Wada et al.

(10) Patent No.: US 8,546,639 B2
(45) Date of Patent: Oct. 1, 2013

(54) URINE SUCTION DEVICE

(75) Inventors: Ichiro Wada, Kagawa (JP); Miou Suzuki, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 142 days.

(21) Appl. No.: 12/867,276

(22) PCT Filed: Nov. 20, 2008

(86) PCT No.: PCT/JP2008/071080
§ 371 (c)(1),
(2), (4) Date: Oct. 28, 2010

(87) PCT Pub. No.: WO2009/101738
PCT Pub. Date: Aug. 20, 2009

(65) Prior Publication Data
US 2011/0040267 A1 Feb. 17, 2011

(30) Foreign Application Priority Data
Feb. 13, 2008 (JP) .................................. 2008-032193

(51) Int. Cl.
*A61M 1/00* (2006.01)
*A61F 13/15* (2006.01)
*A61F 13/20* (2006.01)

(52) U.S. Cl.
USPC .......................... 604/361; 604/317; 604/318

(58) Field of Classification Search
USPC ................. 604/313, 315, 319, 320, 329, 331, 604/347, 378, 379, 380, 385, 381, 382, 383
See application file for complete search history.

(56) References Cited

U.S. PATENT DOCUMENTS

| 4,356,818 A | * | 11/1982 | Macias et al. ................. 128/886 |
| 5,036,859 A | * | 8/1991 | Brown .......................... 600/547 |
| 7,939,706 B2 | * | 5/2011 | Okabe et al. ................. 604/361 |
| 2005/0070861 A1 | | 3/2005 | Okabe et al. |
| 2007/0035405 A1 | | 2/2007 | Wada et al. |
| 2008/0033386 A1 | * | 2/2008 | Okabe et al. ................. 604/378 |

FOREIGN PATENT DOCUMENTS

| JP | 10-230000 A | 9/1998 |
| JP | 2002-055074 A | 2/2002 |
| JP | 2004-267517 A | 9/2004 |
| JP | 2005-102979 A | 4/2005 |
| JP | 2007-044493 A | 2/2007 |

OTHER PUBLICATIONS

International Search Report from corresponding PCT application No. PCT/JP2008/071080, dated Feb. 3, 2009, 4 pages.

* cited by examiner

*Primary Examiner* — Melanie J Hand
*Assistant Examiner* — Mark K Han
(74) *Attorney, Agent, or Firm* — Brinks Hofer Gilson & Lione

(57) ABSTRACT

A urine suction device improved to achieve quick urine which includes a urine receiver unit and a urine detector unit. The urine detector unit includes a pair of electrode assemblies adapted to output a detection signal as soon as it is wetted with urine. The pair of electrode assemblies is sandwiched between a liquid-pervious first sheet and a liquid-pervious second sheet. The first and second sheets are put flat and joined together along joint zones provided outside respective pairs of opposite side edges of the electrode assemblies. Along the respective joint zones, at least one of the first and second sheets has its thickness locally reduced and the first and second sheets are kept in close contact with each other along the joint zones and in the vicinity of the joint zones.

20 Claims, 12 Drawing Sheets

FIG.12
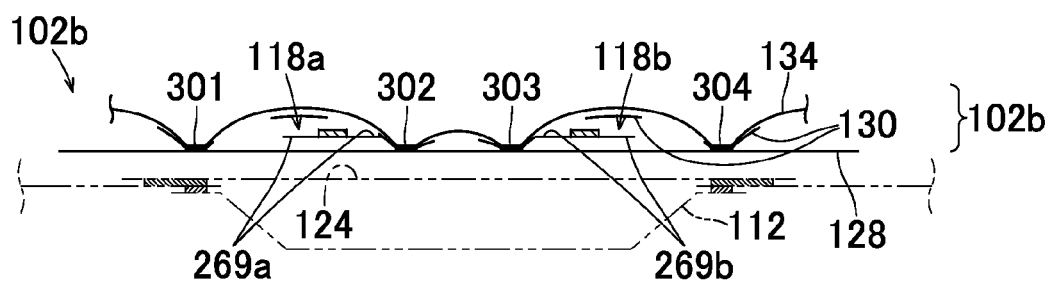
FIG.13
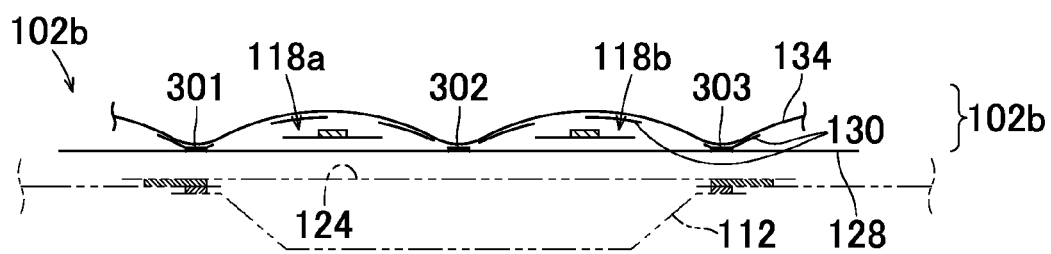
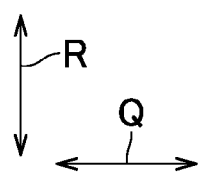

URINE SUCTION DEVICE

RELATED APPLICATION

This application is a 35 U.S.C. §371 national phase filing of International Patent Application No. PCT/JP2008/071080, filed Nov. 20, 2008, through which and to which priority is claimed under 35 U.S.C. §119 to Japanese Patent Application No. 2008-032193, filed Feb. 13, 2008.

TECHNICAL FIELD

The present invention relates to urine suction devices adapted to take care of urination in an automatic fashion and thereby to assist persons for whom it is difficult to control urination timing on their own will or to clean up after urination.

RELATED ART

Among aged and/or sick persons, there are persons for whom it is difficult to control urination timing on their own will or to clean up after urination. To assist these persons suffering from such problem, for example, JP2004-267517A (PATENT DOCUMENT 1) and JP2007-44493A (PATENT DOCUMENT 2) disclose an automatic urine handling apparatus. Generally, such well-known automatic urine handling apparatus comprises a urine suction device having a urine retainer unit wherein the urine suction device is to be put on a user's body and adapted so as to cover urethral orifice and its peripheral region and vacuum suction means such as a suction pump provided separately of the urine retainer unit so that urine collected by the urine retainer unit may be guided into a urine reservoir under action of the vacuum suction means. Air within the hermetically-sealed urine reservoir may be sucked by the suction pump to generate a differential pressure between the urine retainer unit and the urine reservoir and thereby to guide urine within the urine retainer unit into the urine reservoir.

Such known urine suction device further comprises a urine sensor adapted to detect urination and to generate a detection signal on the basis of which the suction pump is actuated. The urine sensor includes, in turn, a pair of electrodes arranged in parallel to and spaced from each other. When urination occurs and these two electrodes are electrically connected to each other by the intermediary of urine, a urine detecting circuit constituted by these electrodes is turned on, actuating the suction pump. These electrodes are sandwiched between a liquid-pervious topsheet and a urine backflow preventing liquid-pervious sheet.
PATENT DOCUMENT 1: JP2004-267517A
PATENT DOCUMENT 2: JP2007-44493A

DISCLOSURE OF THE INVENTION

Problem to be Solved by the Invention

In these well-known urine suction devices, the topsheet and the urine backflow preventing sheet overlap each other around the urine sensor. Urine permeates these sheets overlapping each other into the urine retainer unit of the urine suction device. So far as these two sheets are maintained in contact with each other, interstices of the fibers constituting the respective sheets are reliably filled with urine, so that the urine retainer unit may be depressurized by the vacuum pump to ensure urine staying in the interstices to be quickly sucked. However, if not only the electrodes themselves but also the sheet members supporting these electrodes have unacceptably large thickness and these sheet members are spaced from each other, it will be difficult to fill the fiber interstices of these sheet members and, in consequence, it will be impossible to suck urine filling the fiber interstices quickly into the urine retainer unit.

In view of the problem as has been described above, it is an object of the present invention to improve the known urine suction device so that urine filling the fiber interstices can be quickly sucked into the urine retainer unit.

Measure to Solve the Problem

According to the present invention, there is provided a urine suction device comprising a urine receiver unit adapted to be put on the wearer's body so as to face the wearer's urethral orifice and its peripheral skin and a urination detector unit attached to the urine receiver unit so as to be interposed between the skin and the urine receiver unit and to detect urination from the urethral orifice, the urine receiver unit and the urination detector unit being connected to a vacuum suction means provided separately of them so that the vacuum suction means is actuated on the basis of a detection signal output from the urine detector unit to suck urine into the urine receiver unit.

The urine suction device further comprises: the urine detector unit comprises a pair of electrode assemblies sandwiched between a liquid-pervious first sheet and a liquid-pervious second sheet and extending in parallel in one direction and spaced from each other so as to output the detection signal when the urine detector unit is wetted with urine, and the first and second sheets are put flat and joined together outside respective pairs of opposite side edges of the pair of electrode assemblies so as to form joint zones along which at least one of the first and second sheets are locally thinned and the first and second sheets are kept in close contact with each other along the joint zones and in the vicinity of the joint zones.

According to one preferred embodiment of the present invention, the joint zones are formed along the side edges of the pair of electrode assemblies in the form of plural spots intermittently distributed or in the form of straight lines.

According to another preferred embodiment of the present invention, the joint zones formed between the pair of electrode assemblies are arranged on lines extending in the one direction.

According to still another preferred embodiment of the present invention, the urine detector unit includes any one of at least one liquid-pervious sheet overlapping the first sheet on the side opposite to the pair of electrode assemblies and at least one liquid-pervious sheet overlapping the second sheet on the side opposite to the pair of electrode assemblies, the any one liquid-pervious sheet being also joined to the first sheet or the second sheet along the joint zones so that the first sheet, the second sheet and the any one liquid-pervious sheet are kept in close contact one with another along the joint zones and in the vicinity of the joint zones.

According to yet another preferred embodiment of the present invention, the joint zones are fusion welded zones obtained by fusing and then hardening at least one of the first sheet and the second sheet so that a total thickness of the first and second sheets along the joint zones is smaller than the total thickness in peripheral regions extending around respective the joint zones.

Effect of the Invention

In the urine suction device according to the present invention, the liquid-pervious first sheet and the liquid-pervious second sheet between which the electrode assemblies are sandwiched are put flat and joined together outside the opposite side edges of the electrode assemblies. These liquid-absorbent first and second sheets are kept in close contact with each other not only along the joint zones but also in the vicinity of these joint zones. Consequentially, the presence of the electrode assemblies would not cause the first and second sheets to be spaced from each other and thereby interfere with the desired quick urine suction into the urine receiving unit.

BRIEF DESCRIPTION OF THE DRAWINGS

FIG. 12 View similar to FIG. 10, showing another embodiment of the urine sensor.

FIG. 13 View similar to FIG. 10, showing still another embodiment.

Figure 1:
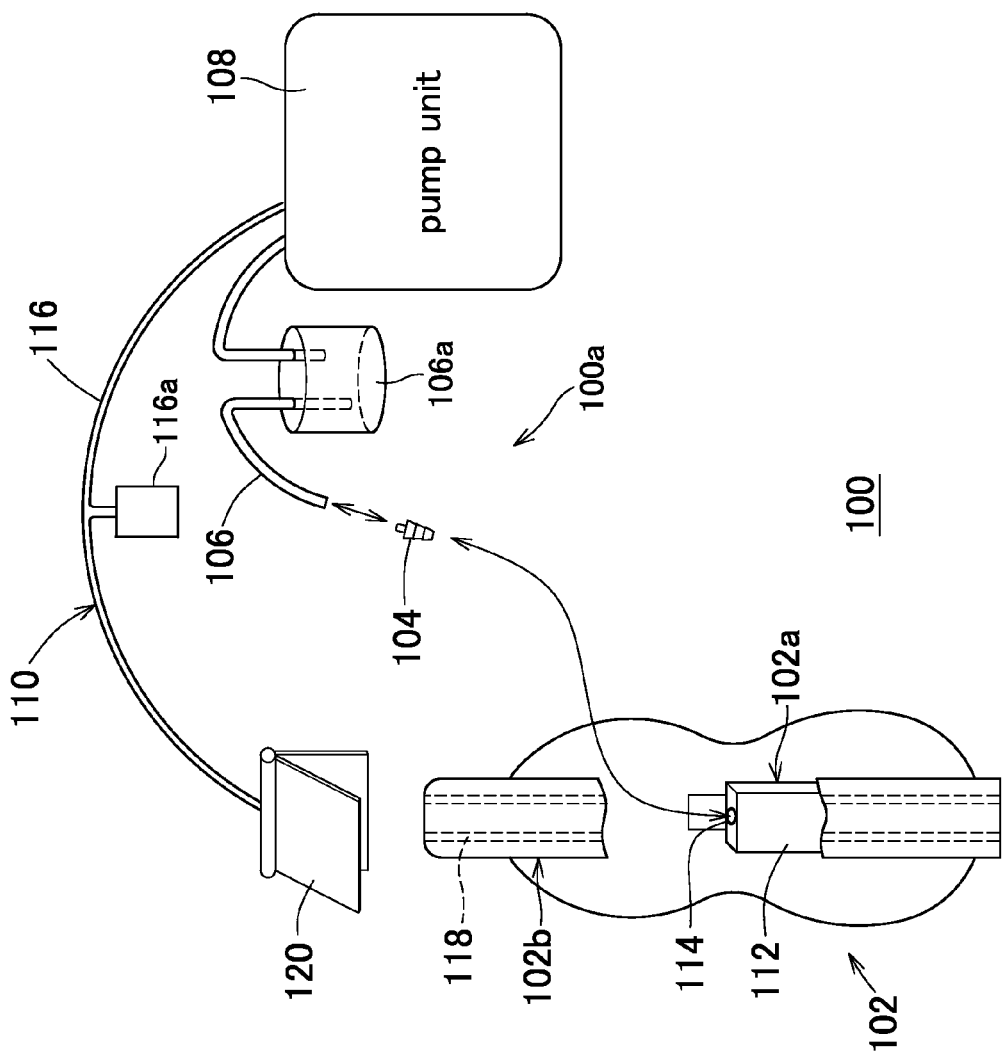
FIG. 1 Schematic diagram illustrating the automatic urine handling apparatus including the urine suction device.

IDENTIFICATION OF REFERENCE NUMERALS USED IN THE DRAWINGS 100a vacuum suction means
102 urine suction device
102a urine receiver unit
112 urine retainer
118a first electrode assembly
118b second electrode assembly
126 liquid-pervious sheet (liquid-dispersible sheet)
128 first sheet (cushion sheet)
130 second sheet (spacer)
132 liquid-pervious sheet (filter)
269a side edge
269b side edge
301 joint zone (first joint zone)
302 joint zone (second joint zone)
303 joint zone (third joint zone)
304 joint zone (fourth joint zone)

DETAILED DESCRIPTION OF THE PREFERRED EMBODIMENTS

Details of a urine suction device will be more fully understood from the description given hereunder with reference to the accompanying drawings.

FIG. 1 is a diagram schematically illustrating an automatic urine handling apparatus 100 comprising a urine suction device 102 according to the present invention and a vacuum suction means 100a combined with the urine suction device 102. The urine suction device 102 has an inner side facing the wearer's skin and an outer side facing a wearer's garment. Referring to FIG. 1, the outer side is illustrated as partially cutaway.

The automatic urine handling apparatus 100 is adapted to collect urine being excreted by a wearer (not shown) in the urine suction device 102 in preparation to disposal thereof. The urine suction device 102 comprises a urine receiver unit 102a put to cover the urethral orifice of the wearer and its peripheral region so as to collect urine being excreted by the wearer and a urine detector unit 102b adapted to detect urination. The vacuum suction means 100a includes a joint member 104 adapted to be connected directly to the urine suction device 102, a urine guide tube 106, a urine reservoir 106a, a pump unit 108 and an electric wiring 116.

The pump unit 108 includes a suction pump (not shown) adapted to be actuated on the basis of a signal transmitted from the urine detector unit 102b via the wiring 116. In the urine suction device 102, a urine retainer 112 of the urine receiver unit 102a is provided in a peripheral wall thereof with a urine outlet 114 to which the urine guide tube 106 is connected via the joint 104. A distal end of the wiring 116 extending from the pump unit 108 is provided with a clip 120 used for electrical connection of electrodes 218a, 218b (See FIGS. 3 and 4) of the urine sensor 118 included in the urine detector unit 102b to the wiring 116. With such automatic urine handling apparatus 100, the urine sensor 118 detects urination and generates a corresponding detection signal which is transmitted to the pump unit 108. Based on this detection signal, the suction pump included in the pump unit 108 is actuated to suck air within the urine reservoir 106a and thereby to suck urine into the urine retainer 112. Urine sucked into the urine retainer 112 is further sucked and collected into the urine reservoir 106a via the joint 104 and the guide tube 106.

Figure 2:
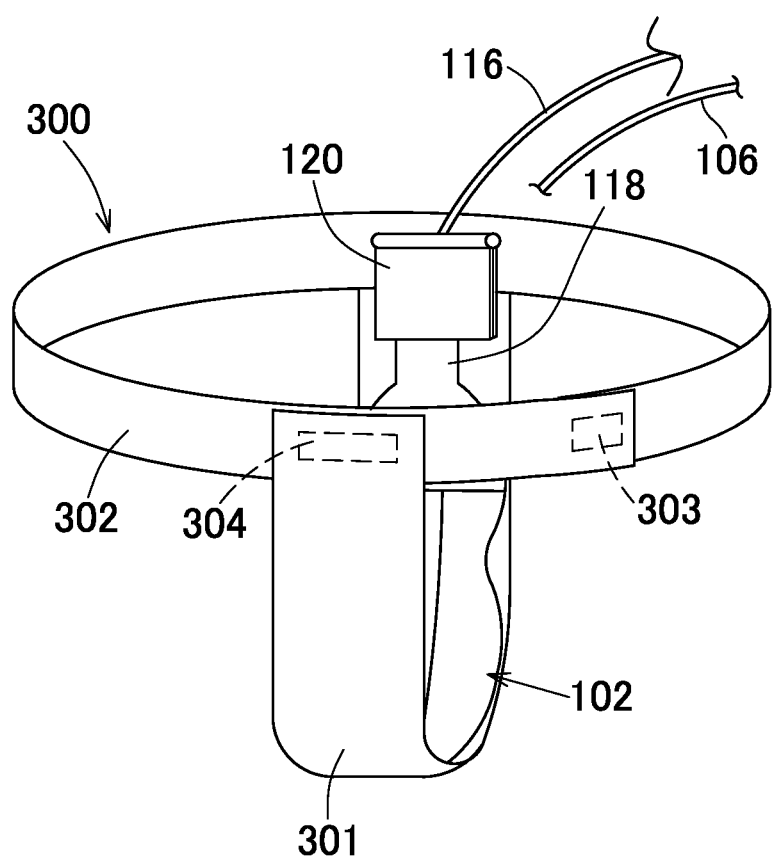
FIG. 2 Diagram illustrating the urine suction device as put on the wearer's body.

FIG. 2 is a diagram exemplarily illustrating how to put the urine suction device 102 on the wearer's body wherein the clip 120 is illustrated to lie on the ventral side. The urine suction device 102 is fixed to an inner side of a crotch belt segment 301 as a part of a T-shaped belt 300, for example, by pressure-sensitive adhesive or a mechanical fastener known by the trade name VELCRO. The urine suction device 102 is put on the wearer's body so that the urine retainer 112 extends for the most part thereof in a longitudinal direction on the wearer's ventral side with its inner side opposed to the wearer's urethral orifice and its peripheral region and with its lower end extending toward the anus along an inner surface of the crotch belt segment so as to describe a gentle curve. In the T-shaped belt 300, opposite ends of a waist belt segment 302 are detachably connected to each other by means of connecting means 303 such as a mechanical fastener while the crotch belt segment 301 is sutured at one end to the waist belt segment 302 and detachably connected at the other end to the waist belt segment 302 by means of a mechanical fastener 304. The chassis for the urine suction device 102 is not limited to the T-shaped belt 300 and the other appropriate means such as open-type diapers, pants-type diapers, diaper covers and incontinent pants may be used as the chassis of this urine suction device 102.

Figure 3:
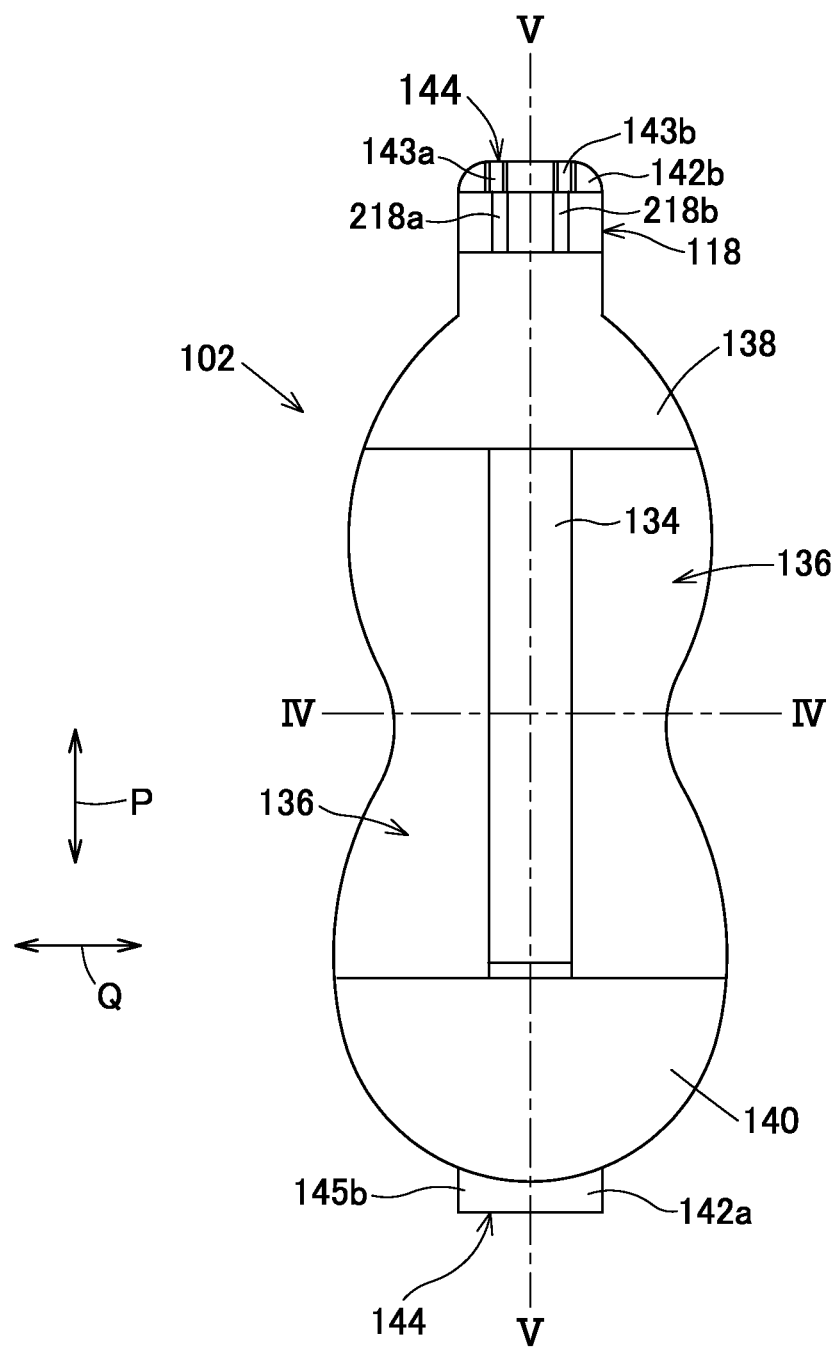
FIG. 3 Plan view of the urine suction device.
Figure 4:
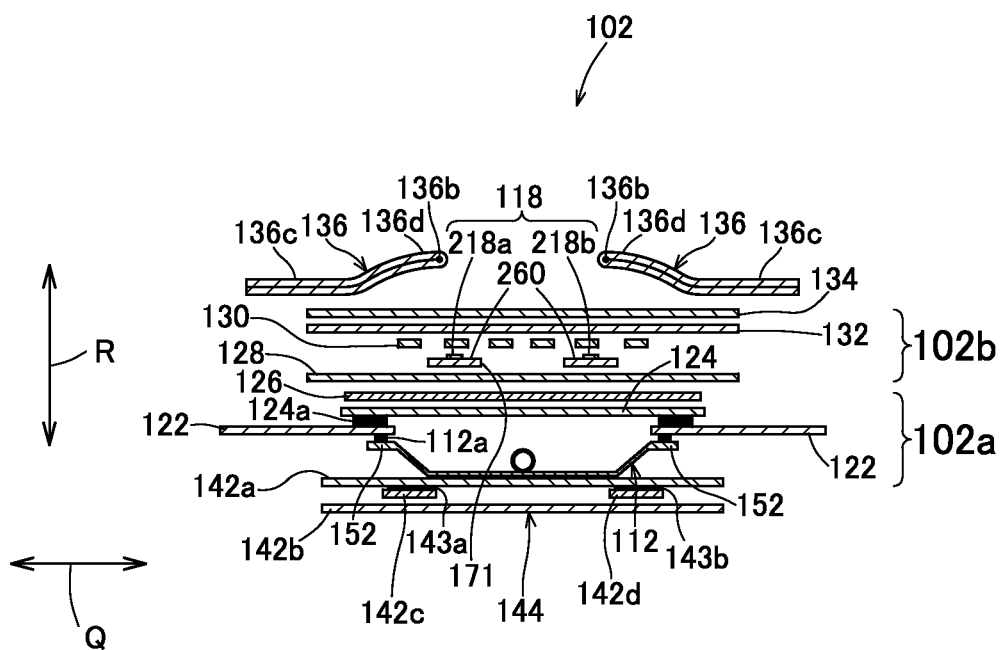
FIG. 4 Sectional view taken along the line IV-IV in FIG. 3.
Figure 5:
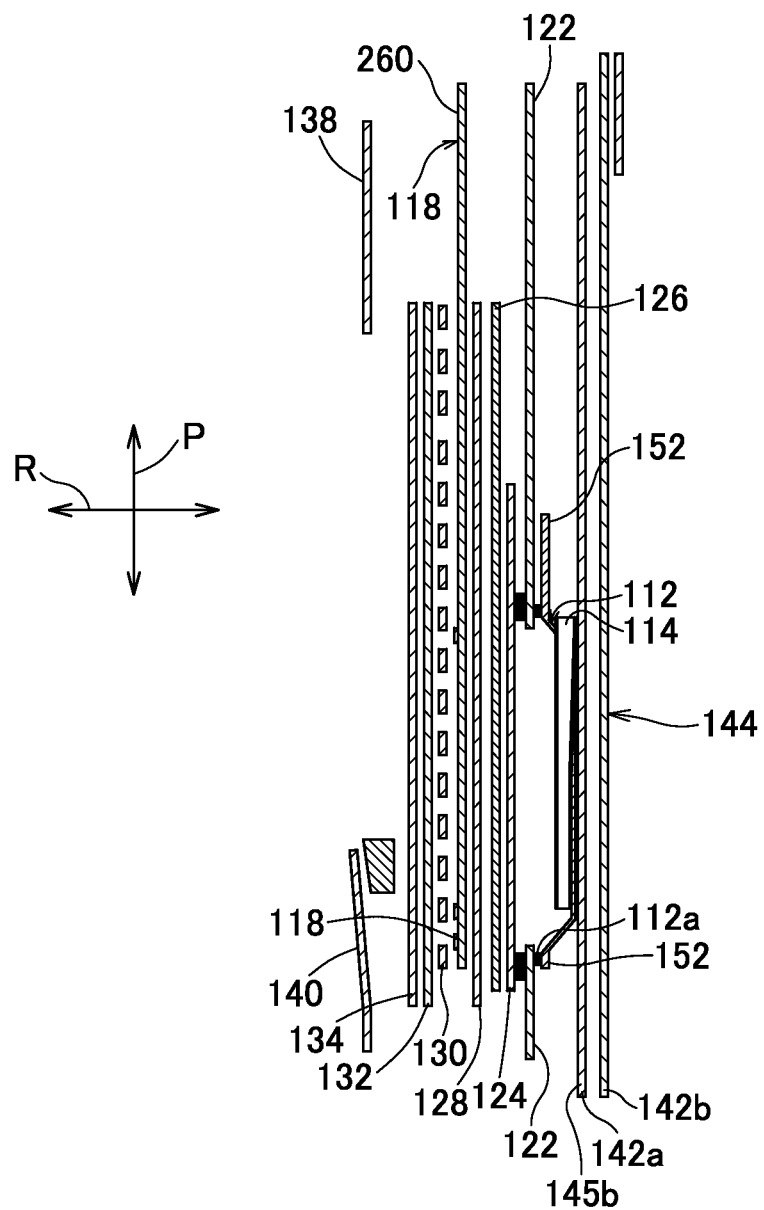
FIG. 5 Sectional view taken along the line V-V in FIG. 3.

FIG. 3 is a plan view showing the inner side of the urine suction device 102, FIG. 4 is a sectional view taken along the line IV-IV in FIG. 3, and FIG. 5 is a sectional view taken along the line V-V in FIG. 3 wherein the respective members overlapping one another in a thickness direction R of the urine suction device 102 are substantially illustrated to be spaced one from another in FIGS. 4 and 5.

The urine suction device 102 has a longitudinal direction P corresponding to the same direction of the wearer's body and a transverse direction Q extending orthogonally to the longitudinal direction P. The urine suction device 102 has a relatively large width in the vicinity of ends opposite in the longitudinal direction P and a relatively small width in a middle as viewed in the direction P. The urine suction device 102 has also the thickness direction R and comprises a plurality of sheet members overlapping one another, i.e., a liquid-impervious leak-preventing sheet 122, a liquid-pervious but air-permeation retardant sheet 124, a liquid-dispersible sheet 126, a cushion sheet 128, the urine sensor 118, a sheet-like spacer 130, a sheet-like filter 132 and a liquid-pervious skin-contact sheet 134 in this order from the bottom as viewed in the thickness direction R. A pair of leak-preventing barriers 136 overlaps the skin-contact sheet 134. The leak-preventing sheet 122, the air-permeation retardant sheet 124 and the liquid-dispersible sheet 126 are integrated with the urine retainer 112 to form the urine receiver unit 102a. The cushion sheet 128, the urine sensor 118, the spacer 130, the filter 132 and the skin-contact sheet 134 overlap one another to form the urine detector unit 102b.

The urine retainer 112 is provided in the form of a tray and made of a soft elastic material such as soft polyethylene or silicon rubber so as to be flexible in the longitudinal direction as well as in the transverse direction Q but well resistant to any deformation due to a negative pressure exerted thereon during urine suction by the suction pump. The leak-preventing sheet 122 is water-tightly bonded to a peripheral flange 152 of the urine retainer 112 by means of adhesive 112a.

The leak-preventing sheet 122 extends outward beyond the urine retainer 112 so as to prevent any amount of urine from leaking out from the urine suction device 102. The leak-preventing sheet 122 may be formed, for example, of a thermoplastic synthetic resin film or a composite sheet consisting of such film and a nonwoven fabric. For the urine suction device 102 of FIG. 1, the leak-preventing sheet 122 is formed of a soft polyethylene film having a thickness of 30 μm. Should the urine suction device 102 requires no leak-preventing property for the periphery of the urine retainer 112, it will be possible to exploit the present invention without use of the leak-preventing sheet 122.

The air-permeation retardant sheet 124 is significantly liquid-pervious but substantially or completely air-impermeable. As will be apparent from FIG. 4, this sheet 124 covers a top opening of the urine retainer 112 and has its peripheral portion bonded to the leak-preventing sheet 122 from above by hot melt adhesive 124a. The urine retainer 112 provided with the air-permeation retardant sheet 124 in this manner is readily put under a negative pressure as soon as the suction pump of the pump unit 108 is actuated and urine collected in the urine retainer 112 can be quickly sucked by the suction pump. As stock materials for the air-permeation retardant sheet 124, for example, an SMS nonwoven fabric consisting of a spun bond nonwoven fabric having a basis weight of 22 g/m$^2$, a melt blown nonwoven fabric having a basis weight of 10 g/m$^2$ and a spun bond nonwoven fabric having a basis weight of 22 g/m$^2$, preferably modified by surfactant to become hydrophilic can be used. On the basis of the result obtained from measurement of air-permeability carried out according to Method A selected from Method for Air-permeability Measuring Methods prescribed in Section 6.27.1 of JIS L 1096, air-permeability of the air-permeation retardant sheet 124 is, in a wet condition, in a range from 0 to 100 cc/cm$^2$/sec, preferably in a range from 0 to 50 cc/cm$^2$/sec. In dry condition, this value is in a range from 20 to 200 cc/cm$^2$/sec, preferably in a range from 20 to 100 cc/cm$^2$/sec, more preferably in a range from 20 to 50 cc/cm$^2$/sec. The term "wet condition" used herein for measurement of the air-permeability refers to a condition in which a moisture content of the air-permeation retardant sheet 124 calculated by a following formula (1) is 100% or higher while the term "dry condition" refers to the condition of this air-permeation retardant sheet 124 after this sheet has been left in a room at a temperature of 20° C. and an RH of 50% for more than 24 hours.

Moisture content=(weight of sheet in a wet condition −weight of sheet in a dry condition)/(weight of sheet in dry condition)   Formula (1)

The liquid-dispersible sheet 126 is formed of a liquid-pervious sheet such as a nonwoven fabric containing hydrophilic fibers such as rayon fibers and serves to disperse urine rapidly over the air-permeation retardant sheet 124 upon urination and thereby to make the air-permeation retardant sheet over an area as large as possible in a wet condition. The air-permeation retardant sheet 124 in such wet condition ensures that a negative pressure is generated within the urine retainer 112 and, in consequence, urine suction into the urine retainer 112 is facilitated. Preferably, the liquid-dispersible sheet 126 is intermittently bonded to the air-permeation retardant sheet 124 to avoid a problem that the liquid-pervious properties of these two sheets would be deteriorated.

The cushion sheet 128 is formed by a liquid-pervious sheet such as thermal bond nonwoven fabric having a basis weight of 20 to 30 g/m$^2$ adapted to promote permeation of urine and thereby to prevent any amount of urine present in the liquid-dispersible sheet 126 and the air-permeation retardant sheet 124 from flowing back toward the urine sensor 118. Furthermore, the sheet-like members such as the urine sensor 118, the spacer 130 and the filter 132 may be previously overlapped upon the cushion sheet 128 to make it possible for the cushion sheet 128 to serve as a carrier member used to hold these sheet-like members at predetermined positions in the urine suction device 102 in the course of manufacturing the urine suction device 102. Preferably, the cushion sheet 128 is intermittently bonded to the liquid-dispersible sheet 126 in order to prevent the liquid-pervious property of these two sheets 128, 126 from being deteriorated.

The urine sensor 118 is obtained, for example, by printing the electrode pair of desired shape on a synthetic resin film with conductive ink and structural details thereof will be described later. The urine sensor 118 may be bonded to the cushion sheet 128.

The spacer 130 is thicker than any other sheet-like members in the urine detector unit 102b and provided in the form of a mesh textured liquid-pervious sheet. In the urine suction device 102, there is possibility that, even after operation of suction, the skin-contact sheet 134 might remain in wet condition due to any amount of urine still staying thereon. In this case, the skin-contact sheet 134 might come in direct or indirect contact with the urine sensor 118, for example, under the wearer's body weight and cause a false operation of the urine sensor 118. The spacer 130 functions as means to keep the urine sensor 118 and the filter 132 spaced from each other and thereby to prevent the false operation of the urine sensor 118. More specifically, the spacer 130 is not responsible for urine suction but water repellent and has an air-permeability as well as a liquid-permeability higher than those of the air permeation retardant sheet 124. The spacer 130 maintains its thickness constant even under the wearer's body weight. Such spacer 130 can be formed by a mesh textured sheet having a thickness of 0.5 to 1 mm made of soft synthetic resin such as vinyl acetate and is preferably bonded to the cushion sheet 128 in a manner that the liquid-permeability of these sheet members might not be adversely affected.

The filter 132 is used to prevent any solid material contained in urine from accumulating on the urine sensor 118 and becoming permanently conductive and, in view of this, the filter 132 is preferably formed by the sheet having air-permeability and liquid-permeability both higher than those of the air-permeation retardant sheet 124 and more preferably formed of a nonwoven fabric. The filter 132 may be permanently bonded to spacer 130 in a manner that the liquid-permeability of these sheet members might not be adversely affected.

The skin-contact sheet 134 overlies the filter 132 and is adapted to face and come in contact with the wearer's urethral orifice and peripheral region thereof as the urine suction device 102 is put on the wearer's body. Such skin-contact sheet 134 may be formed of a soft and liquid-pervious sheet material such as a thermal bond nonwoven fabric having a basis weight of 15 to 25 g/m$^2$. Similarly to the cushion sheet 128, the skin-contact sheet 134 is instantaneously impregnated with urine at an initial stage of urination. The skin-contact sheet 134 is bonded to the filter 132 preferably in the intermittent fashion in order to prevent the liquid-permeability of these sheets 134, 132 from being adversely affected by this bonding treatment. The skin-contact sheet 134 may be hydrophilic or water-repellent.

The leak-preventing barrier 136 is paired in right and left barriers as will be seen in FIGS. 3 and 4 and adapted to prevent any amount of urine might flow on the skin-contact sheet 134 in the transverse direction Q and leak sideways out from the urine suction device 102. The leak-preventing barrier 136 has its outer side edge 136c lying aside toward the outer side edge of the urine suction device 102 and bonded to the skin-contact sheet 134 while its inner side edge 136d lying aside toward the middle zone of the urine suction device 102 is not bonded to the skin-contact sheet 134 and provided with an elastic member 136b (See FIG. 4) such as rubber thread bonded under tension thereto so as to extending in the longitudinal direction P. With the urine suction device 102 being put on the wearer's body, it bows in the longitudinal direction P as will be seen in FIG. 1 under contraction of the elastic member 136b and thereupon the side edge 136d of the leak-preventing barrier 136 is spaced upward from the skin-contact sheet 134. The leak-preventing barrier 136 is formed of a soft thermoplastic synthetic resin film or a composite sheet consisting of such film and a nonwoven fabric and preferably of liquid-impervious nature. As viewed with the urine suction device 102 being flattened (See FIG. 3), upper and lower ends of the leak-preventing barrier 136 are covered with first and second end sheets 138, 140, respectively.

With the urine suction device 102 put on the wearer's body, should defecation occur and the skin-contact sheet 134 be covered with feces, it will become no more possible for the urine suction device 102 to detect urination and/or to carry out the desired task of urine suction. To avoid such undesired situation, the urine suction device 102 is provided with a defecation sensor 144 as illustrated in FIGS. 3, 4 and 5. In the defecation sensor 144, electrodes 143a, 143b are formed on upper surfaces of thermoplastic synthetic resin film 142c, 142d, for example, by aluminum vapor deposition and the film 142c, 142d are covered with cover sheets 142a, 142b, respectively. The cover sheets 142a, 142b are liquid-pervious so that moisture contained in feces may permeate these cover sheets 142a, 142b toward the electrodes 143a, 143b, respectively. In this defecation sensor 144, the electrodes 143a, 143b extend in the longitudinal direction P in parallel to the electrodes 218a, 218b for urination detection and lower ends 145b of these electrodes 143a, 143b as viewed in FIGS. 3 and 5 extend downward beyond the end sheet 140. When the lower ends 145b are soiled with feces, the moisture contained in feces permeates the cover sheets 142a resulting in electrical connection between the electrodes 143a, 143b. In consequence, a power source 116a (See FIG. 1) provided in the wiring 116 generates alarm signal which is transmitted to an alarm system (not shown) included in the pump unit 108. In response to the alarm signal, the alarm system reminds a helper or the like to make desired disposal and to exchange the urine suction device 102 with a fresh one.

Figure 6:
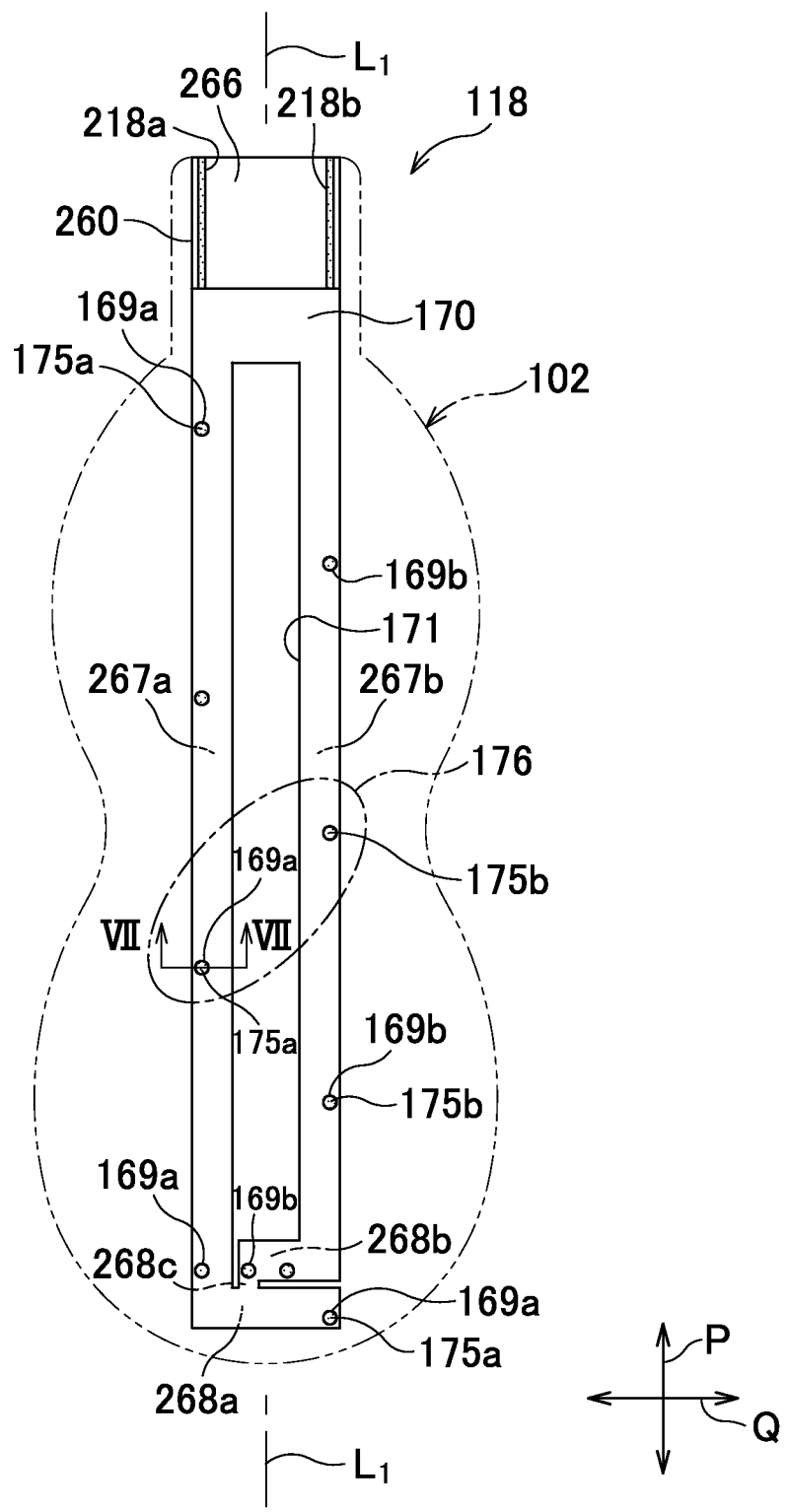
FIG. 6 Plan view of the urine sensor.

FIG. 6 is a plan view of the urine sensor 118 used in the device illustrated by FIGS. 3, 4 and 5, wherein the urine suction device 102 is indicated by imaginary line. The urine sensor 118 comprises a film member 260 formed of a synthetic resin film, a pair of urine detection electrodes 218a, 218b formed on one surface of the film member 260 and insulating coating 170 with which the most part of these electrodes 218a, 218b are coated. The film member 260 is a rectangular member extending in the longitudinal direction P and a middle zone of this rectangular film member 260 as viewed in the transverse direction Q is cut out in the longitudinal direction P so as to form a substantially rectangular opening 171. Such film member 260 has an upper end 266 adapted to hold the clip 120 as seen in upper portion of FIG. 6, lateral zones 267a, 267b extending downward from the upper end 266 on both sides of a center line $L_1$-$L_1$ which dissects the dimension of the urine sensor 118 as viewed in the transverse direction, and lower ends 268a, 268b extending downward from the lateral zones 267a, 267b, respectively. The lower end 268a and the lower end 268b are connected to each other by a hookup 268c. At the upper end 266 of the film member 260, the electrodes 218a, 218b are exposed. The lateral zones 267a, 267b and the lower ends 268a, 268b are coated with the insulating coating 170 for the most part thereof, leaving a plurality of circular spots as non-coated regions 169a, 169b in which urine detecting region 175a or 175b of the electrode 218a or 218b is exposed.

Figure 7:
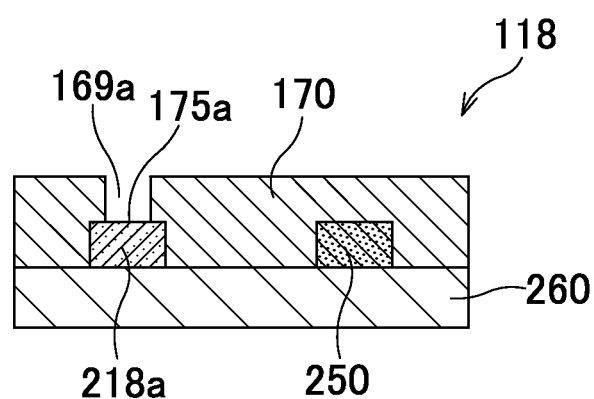
FIG. 7 Sectional view taken along the line VII-VII in FIG. 6.

FIG. 7 is a sectional view taken along the line VII-VII in FIG. 6. The film member 260 is formed on its upper side as viewed in FIG. 7 with, in addition to the electrode 218a for urine detection, a circuit 250 for detection of breaking. The urine detection region 175a of the electrode 218a is exposed in the non-coated region 169a while the circuit 250 is entirely covered with the insulating coating 170.

Figure 8:
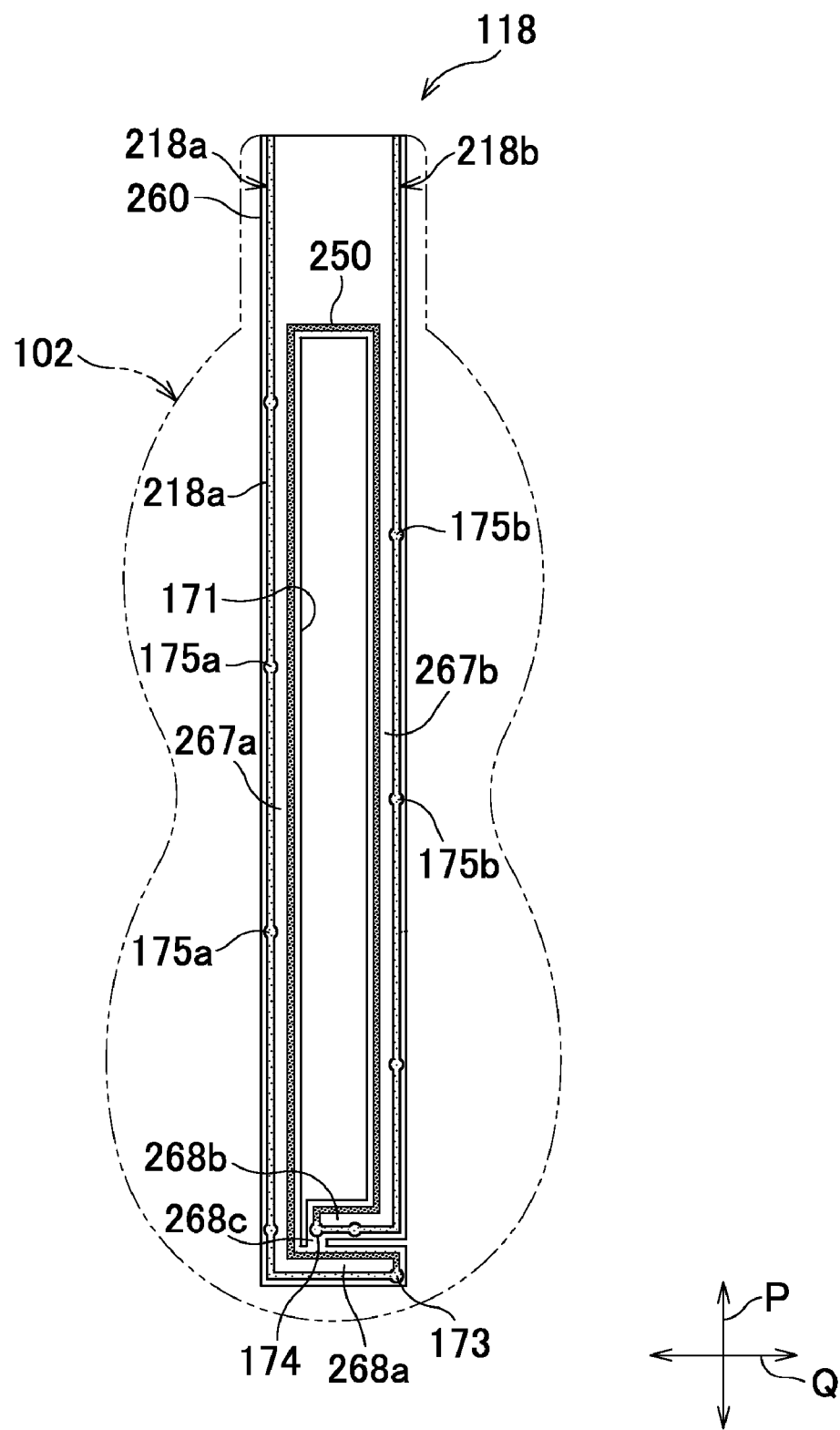
FIG. 8 Plan view of the urine sensor having its insulating coating removed.

FIG. 8 is a plan view showing the urination sensor 118 with the insulating coating 170 peeled off. On one surface of the film member 260, the urine detecting electrode 218a extends substantially in an L-shape along the lateral zone 267a and the lower end 268a. The other urine detecting electrode 218b extends substantially in a reversed L-shape along the lateral zone 267b and the lower end 268b. The circular regions 175a, 175b formed in these electrodes 218a, 218b are exposed in the non-coated regions 169a, 169b as seen in FIG. 6. Between these electrodes 218a, 218b, the breaking detector circuit 250 which is electrically connected with the respective lower ends 173, 174 of the urine detecting electrodes 218a, 218b and extends along the peripheral edge of the opening 171 as illustrated.

In the urine sensor 118 as has been described above, the film member 260 is preferably formed of a polyester film having a thickness of 50 to 100 µm. The electrodes 218a, 218b may be obtained by printing them in desired shapes on the film member 260 with conductive ink or conductive coating material. The conductive ink or the conductive coating material may contain, for example, carbon black in 3 to 7% by weight, artificial graphite such as carbon graphite in 10 to 30% by weight and an appropriate quantity of silver pigment. Preferably, each of the electrode 218a, 218b is configured to have a width of 0.5 to 2.0 mm and a resistance value of 150 KΩ or lower wherein each of the non-coated regions 169a, 169b has a diameter of 1 to 2 mm. The breaking detector circuit 250 may be obtained, for example, by printing them in a desired shape on the film member 260 with ink containing carbon black in 3 to 7% by weight and artificial graphite in 5 to 10% by weight. It is essential for this circuit 250 to exhibit a resistance value substantially higher than a resistance value exhibited by the urine detecting electrodes 218a, 218b and preferably has a width of 0.3 to 1 mm and a resistance value of 2 to 10 MΩ.

In the case of the urine suction device 102 using the urine sensor 118 of FIG. 6, the power source 116a contained in the wiring 116 supplies weak current A so as to flow on a steady basis between electrodes 218a, 218b and the circuit 250 electrically connected to them. So far as passage of the current A in an electric circuit 110 inclusive of the wiring 116 is detected, the urine detecting electrodes 218a, 218b are determined to be normal. If the current A can not be detected, on the contrary, it is determined that there is some kind of trouble such as breaking in the urine detecting electrodes 218a, 218b. In this case, the pump unit 108 may output a signal to the helper and remind exchange of the urine sensor 118. If a region surrounded by the imaginary line 176 in FIG. 6 is wetted with urine, urine will flow into the non-coated regions 169a, 169b provided in the lateral zones 267a, 267b and then come in contact with the urine detecting regions 175a, 175b, respectively. As a result, the electrode 218a in the lateral zone 267a and the electrode 218b in the lateral zone 267b are electrically connected with each other by the intermediary of urine. When a resistance across urine present between the electrodes 218a, 218b becomes lower than a resistance across the circuit 250, the current flows no more across the circuit 250 having a resistance but flows across urine having a resistance decreased. When a value of the current B flowing across urine becomes higher than a value of the current A flowing across the circuit 250, the electric circuit 110 can detect occurrence of urination on the basis of an abrupt change in the current or an abrupt change in voltage or resistance reflecting the change in the current. In response to the signal generated on the basis of such change, the pump unit 108 actuates the suction pump to suck urine and turns off the suction pump when the resistance across the electrodes 218a, 218b increases until the predetermined level.

While the non-coated regions 169a, 169b adapted to expose the urine detecting regions 175a, 175b of the urine sensor 118 in the embodiment illustrated by FIG. 6 are formed in the lateral zones 267a, 267b in asymmetrically about the center line $L_1$-$L_1$, it is possible to provide these non-coated regions 169a, 169b in symmetrically about the center line $L_1$-$L_1$. According to the embodiment illustrated by FIG. 6, a plurality of the non-coated regions 169a, 169b are provided at the lower ends 268a, 268b of the film member 260 and in the vicinity thereof closely one to another. Such unique arrangement of the non-coated regions 169a, 169b is advantageous in that, even if urine immediately after urination is rapidly dispersed from above downward as viewed in FIG. 6 rather than flowing toward the air-permeability retardant sheet 124, the urine suction device 102 can quickly suck such amount of urine. However, it will be appreciated that the pattern in which the non-coated regions 169a, 169b are distributed is not limited to that adopted by this particular embodiment and these non-coated regions may be appropriately located in the lateral zones 267a, 267b taking account of the wearer's posture when the urine suction device 102 is put on the wearer's body.

Figure 9:
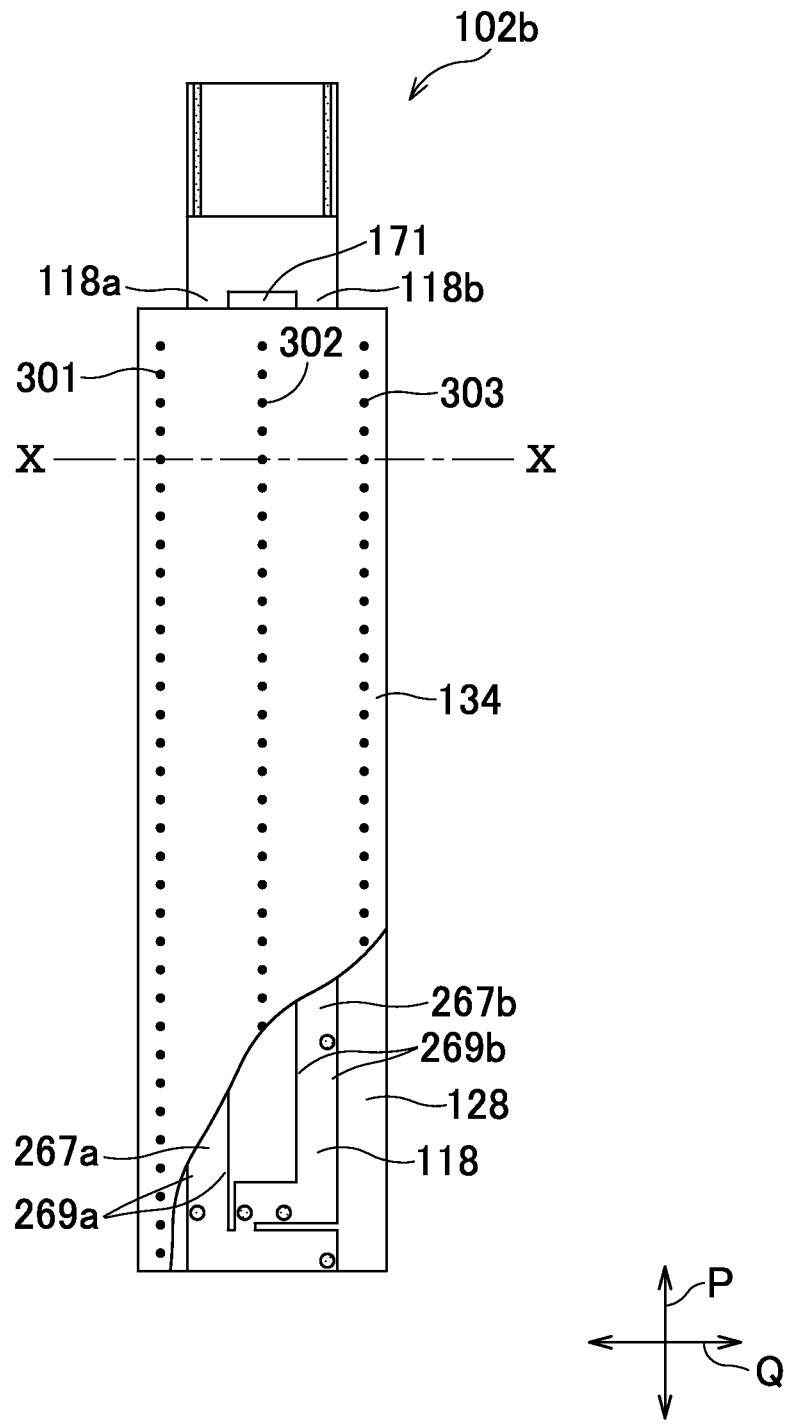
FIG. 9 Partially cutaway plan view of the urine sensor.
Figure 10:
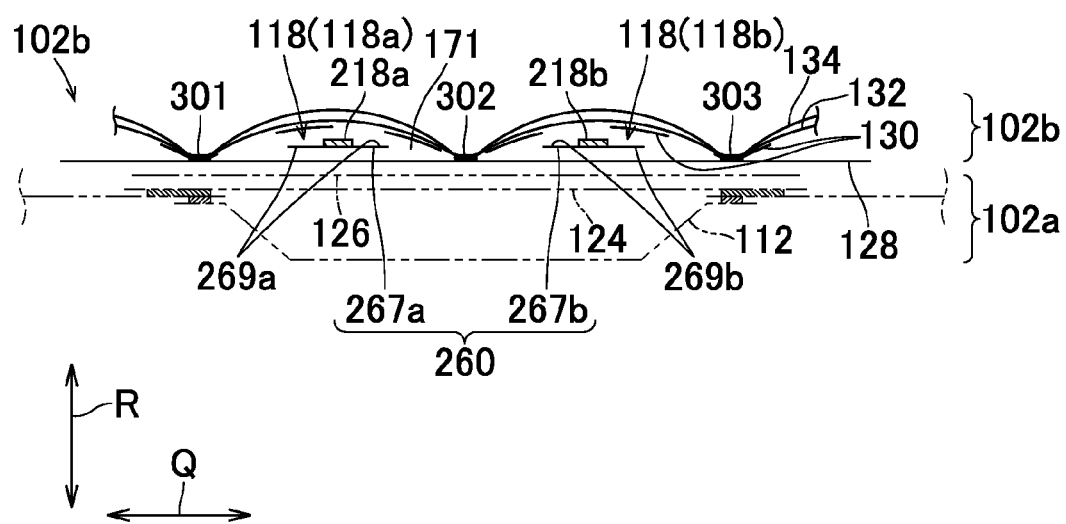
FIG. 10 Sectional view taken along the line X-X in FIG. 9.

FIG. 9 is a plan view of the urine detector unit 102b and FIG. 10 is a schematic sectional view taken along a line X-X in FIG. 9 wherein the urine receiver unit 102a is indicated by imaginary lines in FIG. 10. As will be seen in FIG. 6 through 8, the urine sensor 118 of the urine detector unit 102b is provided in the paired lateral zones 267a, 267b of the film member 260 spaced from each other in the transverse direction Q and extending in parallel to each other in the longitudinal direction P with the electrodes 218a, 218b, respectively. A first electrode assembly 118a of the urine sensor 118 comprising the lateral zone 267a and the electrode 218a is sandwiched by the cushion sheet 128 and the spacer 130. Portions of these cushion sheet 128 and the spacer 130 extending beyond opposite side edges 269a of the first electrode assembly 118a are put flat and bonded together along first and second zones 301, 302 defined outside the respective side edges 269a. The filter 132 and the skin-contact sheet 134 both overlapping the spacer 130 are bonded not only to each other but also to the cushion sheet 128 and the spacer 130 along these first and second joint zones 301, 302. Portions of these cushion sheet 128 and the spacer 130 extending beyond opposite side edges 269b of the second electrode assembly 118b are put flat and bonded together along second and third joint zones 302, 303 defined outside the respective side edges 269b. The filter 132 and the skin-contact sheet 134 both overlapping the spacer 130 are bonded not only to each other but also to the cushion sheet 128 and the spacer 130 along these second and third joint zones 302, 303.

Along the first, second and third joint zones 301, 302, 303, the sheet members 128, 130, 132, 134 overlapping one another are joined together by fusion or adhesion and in close contact one with another not only along these joint zones 301, 302, 303 but also in the vicinity of these joint zones 301, 302, 303. The term "vicinity" used herein should be construed as an area extending at least 3 mm outside the periphery of each joint zone. According to a more preferred embodiment of the first, second and third joint zones 301, 302, 303, the thickness thereof is compressed so that at least the cushion sheet 128 or the spacer 130 of the sheet members 128, 130, 132, 134 may be relatively thin, preferably it is compressed to the range of ⅔ to ⅒ of the thickness in a no-joint zone extending 5 mm outside the joint zone. In the case of the first, second and third joint zones 301, 302, 303 obtained by locally compressing the sheet members 128, 130, 132, 134 and simultaneously fusing one or more of these sheet members, for example, a thickness of the spacer 130 which is thicker than the remaining sheet members may be reduced along the first, second and third joint zones 301, 302, 303 to enhance a degree of close contact among the sheet members 128, 130, 132, 134 in the vicinity of these joint zones 301, 302, 303. In other words, by fusing the sheet members 128, 130, 132, 134 overlapping one another together at common zones under pressure, total thickness of these sheet members 128, 130, 132, 134 can be effectively reduced. Such method is effective also to keep the sheet members in close contact one with another in the vicinity of the first, second and third joint zones 301, 302, 303. In the case of the first, second and third joint zones 301, 302, 303 obtained by use of adhesive, it is advantageously not essential for the sheet members 128, 130, 132, 134 to contain thermally fusible material. While it is not shown, the sheet members 128, 130, 132, 134 may be intermittently joined together at further zones in addition to the first, second and third joint zones 301, 302, 303 to prevent these sheet members 128, 130, 132, 134 from being displaced from one another.

According to an embodiment of the urine detector unit 102b wherein the cushion sheet 128, the spacer 130, the filter 132 and the skin-contact sheet 134 are joined along the first, second and third joint zones 301, 302, 303 provided outside the respective pairs of opposite side edges 269a, 269b of the first and second electrode assemblies 118a, 118b, the cushion sheet 128, the spacer 130, the filter 132 and the skin-contact sheet 134 are reliably kept in close contact one with another in the vicinity of the first, second and third joint zones 301, 302, 303 even when the cushion sheet 128 and the spacer 130 are apt to be spaced from each other due to a fact that a dimension of the film member 260 or the electrodes 218a, 218b in the thickness direction R is relatively large or a dimension of the opening 171 in the transverse direction Q is relatively small. So far as the spacer 130 which is mesh-textured and having a relatively high thickness among the sheet members and no ability of urine suction is in sufficiently compressed state, the other sheet members 128, 132, 134 can be kept in close contact one with another. Urine discharged onto the skin-contact sheet 134 moves under a suction force of the vacuum suction means 100a to pass through the fiber interstices of the sheet members 134, 132, 128 being in close contact one with another and the meshes of the spacer 130 in this order and then to pass through the air-permeability retardant sheet 124 into the urine retainer 112. The respective sheet members 134, 132, 128 may be provided in the form of fibrous assemblies such as a nonwoven fabric, more preferably in the form of hydrophilic fibrous assemblies to promote movement of urine toward the urine retainer 112 under capillary action in fibrous interstices in these sheet members 134, 132, 128 being in close contact one with another. Referring to FIG. 9, the first, second and third joint zones 301, 302, 303 respectively provided in the form of a plural spots intermittently arranged on a line in the longitudinal direction P preferably in a manner that these joint zones do not disturb movement of urine in the transverse direction B.

In the urine suction device 102 according to the present invention, as will be apparent from FIG. 10, the first electrode assembly 118a and the second electrode assembly 118b are spaced from each other, for example, by 5 to 15 mm in the transverse direction Q and thereby form the opening 171. Consequentially, the cushion sheet 128 and the spacer 130 are opposed to each other in the opening 171 and can be joined together outside the respective pairs of opposite side edges 269a, 269b of the electrode assemblies 118a, 118b. It should be appreciated that the second joint region 302 in the form of plural spots arranged on a line serves for the first electrode assembly 118a as well as the second electrode assembly 118b. Referring to FIG. 10, while the cushion sheet 128 and the dispersing sheet 126 may be joined together along the first, second and third joint zones 301, 302, 303, these two sheets 128, 126 can be kept in close contact with each other so far as the urine suction device 102 is on the wearer's body even if these two sheets 128, 126 are not joined along the first, second and third joint zones 301, 302, 303.

Figure 11:
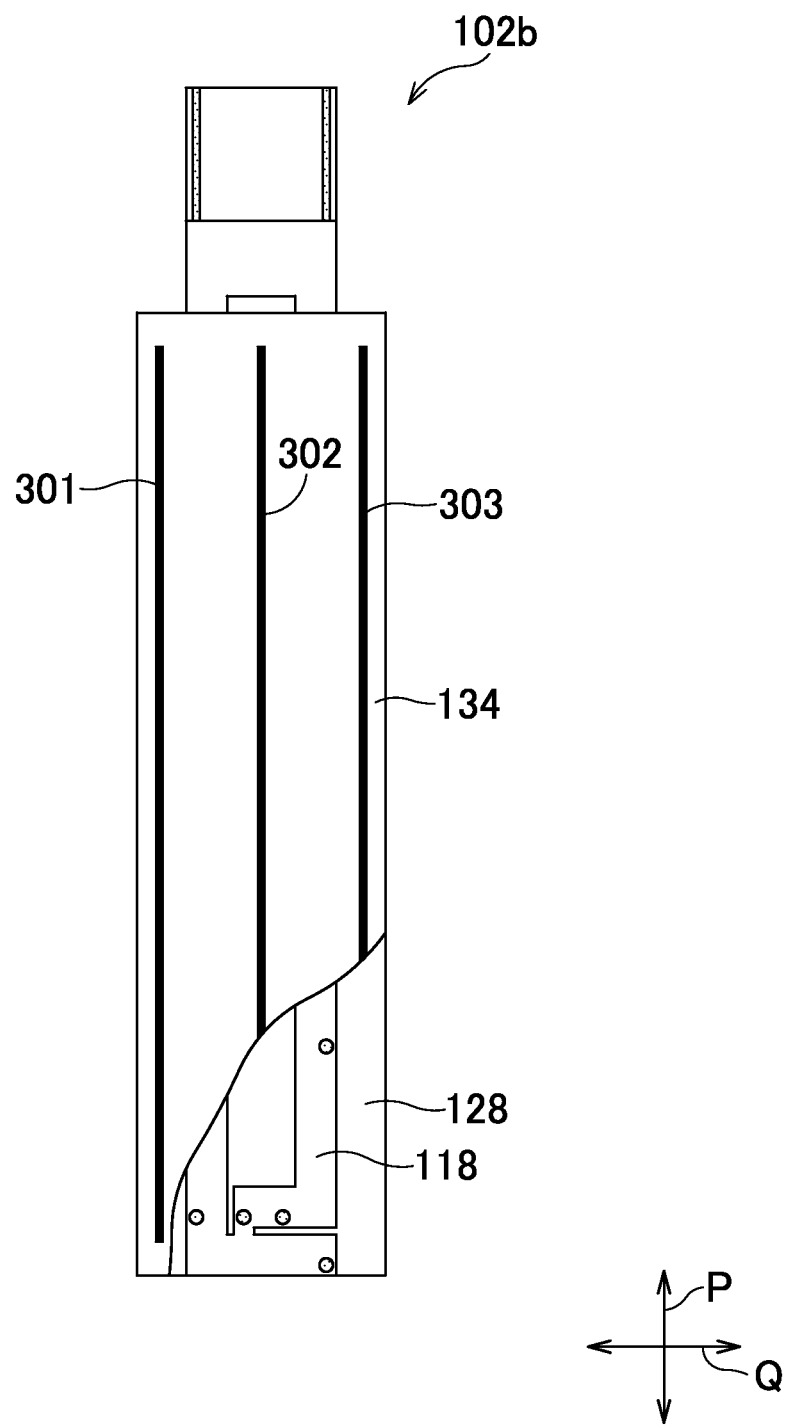
FIG. 11 View similar to FIG. 9, showing one embodiment of the urine sensor.

FIG. 11 is a view similar to FIG. 9, illustrating an alternative embodiment of the present invention. In the case of the urine detector unit 102 illustrated by FIG. 11, each of the first, second and third joint zones 301, 302, 303 is provided in the form of a single line or belt extending in the longitudinal direction P and preferably has a length corresponding to at least ½ of the length of the first and second electrode assemblies 118a, 118b. While these first, second and third joint zones 301, 302, 303 certainly obstruct movement of urine in the transverse direction Q, these continuous linear joint zones ensure the sheet members 128, 130, 132, 134 to be kept in close contact one with another over a large area and promote movement of urine from the urine detector unit 102b toward the urine receiver unit 102a.

FIG. 12 is a view similar to FIG. 10, illustrating still another embodiment of the present invention. The urine detector unit 102b according the embodiment illustrated therein is distinguished from the embodiment illustrated in FIG. 10 in that neither the dispersing sheet 126 nor the filter 132 is included and the air-permeability retardant sheet 124 contains, in addition to the thermoplastic synthetic fibers, hydrophilic fibers such as rayon fibers and thereby serves also as the dispersing sheet 126 of FIG. 10. Regarding the filter 132, the nonwoven fabric used to form the skin-contact sheet 134 has fiber interstices appropriately narrowed so that the skin-contact sheet 134 may function also as the filer 132 used in the embodiment of FIG. 10. Referring to FIG. 12, the cushion sheet 128, the spacer 130 and the skin-contact sheet 134 are joined together outside the side edges 269a of the first electrode assembly 118a along the first joint zone 301 and the second joint zone 302 and outside the side edges 269b of the second electrode assembly 118b along the third joint zone 303 and the fourth joint zone 304. While not illustrated, these first, second, third and fourth joint zones 301, 302, 303, 304 are intermittently provided in the longitudinal direction P. The second joint zone 302 and the third joint zone 303 are provided between the first electrode assembly 118a and the second electrode assembly 118b. The first, second, third and fourth joint zones 301, 302, 303, 304 exemplarily illustrated in FIG. 12 are preferably adopted when a dimension by which the first and second electrode assemblies 118a, 118b are spaced from each other is relatively large.

FIG. 13 also is a view similar to FIG. 10, illustrating yet another embodiment of the present invention. The urine detector unit 102b in the embodiment illustrated herein comprises the air-permeability retardant sheet 124, the cushion sheet 128, the spacer 130 and the skin-contact sheet 134 all of which are similar to them in the embodiment illustrated in FIG. 12. While the cushion sheet 128 and the spacer 130 are joined to each other along the first, second an third joint zones 301, 302, 303, the skin-contact sheet 134 is not joined to the spacer 130 along these joint zones 301, 302, 303. The skin-contact sheet 134 is joined along its peripheral edge (not shown) to the spacer 130 or the cushion sheet 128 overlapping the peripheral edge. If the skin-contact sheet is sufficiently soft to come easily in contact with the spacer 130, the present invention may be implemented in a manner that merely a pair of sheets sandwiching therebetween the first electrode assembly 118a as well as a pair of sheets sandwiching the second electrode assembly 118b are respectively joined together to assure that the respective pairs of sandwiching sheets can be maintained joined together and prevented from being spaced from each other.

The invention claimed is:

1. A urine suction device comprising:
   a urine receiver unit adapted to be put on the wearer's body so as to face the wearer's urethral orifice and its peripheral skin; and
   a urine detector unit attached to said urine receiver unit adapted to be interposed between said skin and said urine receiver unit and to detect urine from said urethral orifice,
   wherein said urine receiver unit and said urine detector unit are connected to a vacuum suction means provided separately of them so that said vacuum suction means is actuated on the basis of a detection signal output from said urine detector unit to suck urine into said urine receiver unit,
   said urine detector unit comprising a pair of electrode assemblies sandwiched between a cushion sheet and a spacer that are liquid-pervious and extending in parallel in one direction and spaced from each other so as to output said detection signal when said urine detector unit is wetted with said urine;

said cushion sheet is interposed between said pair of electrode assemblies and said urine receiver unit, and said spacer is interposed between said pair of electrode assemblies and said skin;

said cushion sheet and said spacer are put flat and joined together about outermost side edges of said pair of electrode assemblies so as to form joint zones along which said cushion sheet and said spacer are locally thinned and said spacer is water repellent so as not to suck urine; and said cushion sheet and said spacer are kept in close contact with each other along said joint zones and in the vicinity of said joint zones.

2. The urine suction device as defined by claim 1, wherein said joint zones are formed along said outermost side edges of said pair of electrode assemblies in the form of plural spots intermittently distributed or in a form of straight lines.

3. The urine suction device as defined by claim 2, wherein said joint zones comprise joint zones that are formed between said pair of electrode assemblies are arranged on lines extending in said one direction.

4. The urine suction device as defined by claim 3, wherein said urine detector unit includes:
  a filter and a skin-contact sheet that are liquid-pervious and overlapping said spacer on the side opposite to said pair of electrode assemblies; and
  a liquid-dispersible sheet overlapping said cushion sheet on the side opposite to said pair of electrode assemblies, said filter and said skin-contact sheet being also joined to said cushion sheet and said spacer along said joint zones so that said cushion sheet, said spacer, said skin-contact sheet, and said filter are kept in close contact one with another along said joint zones and in the vicinity of said joint zones.

5. The urine suction device as defined by claim 4, wherein said joint zones are fusion welded zones obtained by fusing and then hardening at least one of said cushion sheet and said spacer so that a total thickness of said cushion sheet and spacer along said joint zones is smaller than a total thickness of said cushion sheet and spacer in peripheral regions extending around respective said joint zones.

6. The urine suction device as defined by claim 3, wherein said joint zones are fusion welded zones obtained by fusing and then hardening at least one of said cushion sheet and said spacer so that a total thickness of said cushion sheet and spacer along said joint zones is smaller than a total thickness of said cushion sheet and spacer in peripheral regions extending around respective said joint zones.

7. The urine suction device as defined by claim 3, wherein said urine detector unit includes:
  a skin-contact sheet that is liquid-pervious and overlapping said cushion sheet on the side opposite to said pair of electrode assemblies; and
  said skin-contact sheet being also joined to said cushion sheet or said spacer along said joint zones so that said cushion sheet, said spacer, and said skin-contact sheet are kept in close contact one with another along said joint zones and in the vicinity of said joint zones.

8. The urine suction device as defined by claim 2, wherein said urine detector unit includes:
  a filter and a skin-contact sheet that are liquid-pervious and overlapping said spacer on the side opposite to said pair of electrode assemblies; and
  a liquid-dispersible sheet overlapping said cushion sheet on the side opposite to said pair of electrode assemblies, said filter and said skin-contact sheet being also joined to said cushion sheet and said spacer along said joint zones so that said cushion sheet, said spacer, said skin-contact sheet, and said filter are kept in close contact one with another along said joint zones and in the vicinity of said joint zones.

9. The urine suction device as defined by claim 8, wherein said joint zones are fusion welded zones obtained by fusing and then hardening at least one of said cushion sheet and said spacer so that a total thickness of said cushion sheet and spacer along said joint zones is smaller than a total thickness of said cushion sheet and spacer in peripheral regions extending around respective said joint zones.

10. The urine suction device as defined by claim 2, wherein said joint zones are fusion welded zones obtained by fusing and then hardening at least one of said cushion sheet and said spacer so that a total thickness of said cushion sheet and spacer along said joint zones is smaller than a total thickness of said cushion sheet and spacer in peripheral regions extending around respective said joint zones.

11. The urine suction device as defined by claim 2, wherein said urine detector unit includes:
  a skin-contact sheet that is liquid-pervious and overlapping said cushion sheet on the side opposite to said pair of electrode assemblies; and
  said skin-contact sheet being also joined to said cushion sheet or said spacer along said joint zones so that said cushion sheet, said spacer, and said skin-contact sheet are kept in close contact one with another along said joint zones and in the vicinity of said joint zones.

12. The urine suction device as defined by claim 1, wherein said joint zones are formed between said pair of electrode assemblies and are arranged on lines extending in said one direction.

13. The urine suction device as defined by claim 12, wherein said urine detector unit includes:
  a filter and a skin-contact sheet that are liquid-pervious and overlapping said spacer on the side opposite to said pair of electrode assemblies; and
  a liquid-dispersible sheet overlapping said cushion sheet on the side opposite to said pair of electrode assemblies, said filter and said skin-contact sheet being also joined to said cushion sheet and said spacer along said joint zones so that said cushion sheet, said spacer, said skin-contact sheet, and said filter are kept in close contact one with another along said joint zones and in the vicinity of said joint zones.

14. The urine suction device as defined by claim 13, wherein said joint zones are fusion welded zones obtained by fusing and then hardening at least one of said cushion sheet and said spacer so that a total thickness of said cushion sheet and spacer along said joint zones is smaller than a total thickness of said cushion sheet and spacer in peripheral regions extending around respective said joint zones.

15. The urine suction device as defined by claim 12, wherein said joint zones are fusion welded zones obtained by fusing and then hardening at least one of said cushion sheet and said spacer so that a total thickness of said cushion sheet and spacer along said joint zones is smaller than a total thickness of said cushion sheet and spacer in peripheral regions extending around respective said joint zones.

16. The urine suction device as defined by claim 12, wherein said urine detector unit includes:
  a skin-contact sheet that is liquid-pervious and overlapping said cushion sheet on the side opposite to said pair of electrode assemblies; and
  said skin-contact sheet being also joined to said cushion sheet or said spacer along said joint zones so that said cushion sheet, said spacer, and said skin-contact sheet are kept in close contact one with another along said joint zones and in the vicinity of said joint zones.

17. The urine suction device as defined by claim 1, wherein said urine detector unit includes:
- a filter and a skin-contact sheet that are liquid-pervious and overlapping said spacer on the side opposite to said pair of electrode assemblies; and
- a liquid-dispersible sheet overlapping said cushion sheet on the side opposite to said pair of electrode assemblies, said filter and said skin-contact sheet being also joined to said cushion sheet and said spacer along said joint zones so that said cushion sheet, said spacer, said skin-contact sheet, and said filter are kept in close contact one with another along said joint zones and in the vicinity of said joint zones.

18. The urine suction device as defined by claim 17, wherein said joint zones are fusion welded zones obtained by fusing and then hardening at least one of said cushion sheet and said spacer so that a total thickness of said cushion sheet and spacer along said joint zones is smaller than a total thickness of said cushion sheet and spacer in peripheral regions extending around respective said joint zones.

19. The urine suction device as defined by claim 1, wherein said joint zones are fusion welded zones obtained by fusing and then hardening at least one of said cushion sheet and said spacer so that a total thickness of said cushion sheet and said spacer along said joint zones is smaller than a total thickness of said cushion sheet and said spacer in peripheral regions extending around respective said joint zones.

20. The urine suction device as defined by claim 1, wherein said urine detector unit includes:
- a skin-contact sheet that is liquid-pervious and overlapping said cushion sheet on the side opposite to said pair of electrode assemblies; and
- said skin-contact sheet being also joined to said cushion sheet or said spacer along said joint zones so that said cushion sheet, said spacer, and said skin-contact sheet are kept in close contact one with another along said joint zones and in the vicinity of said joint zones.

* * * * *

UNITED STATES PATENT AND TRADEMARK OFFICE
CERTIFICATE OF CORRECTION

PATENT NO.            : 8,546,639 B2                              Page 1 of 1
APPLICATION NO.  : 12/867276
DATED                    : October 1, 2013
INVENTOR(S)         : Ichiro Wada and Miou Suzuki It is certified that error appears in the above-identified patent and that said Letters Patent is hereby corrected as shown below:

Title page

In the Abstract

In column 2, item (57), the first line between "urine" and "which" insert --suction--.

In the Specification

In column 11, line 29, delete "B" and substitute --Q--.

Signed and Sealed this
Sixteenth Day of August, 2016

Michelle K. Lee
*Director of the United States Patent and Trademark Office*